DEFENSIVE PUBLICATION

UNITED STATES PATENT AND TRADEMARK OFFICE

Published at the request of the applicant or owner in accordance with the Notice of Dec. 16, 1969, 869 O.G, 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED DECEMBER 2, 1975

941 O.G. 10

T941,025
INSECTICIDAL DEVICE
Frank H. Dowell, Concord, Calif., assignor to The Dow Chemical Company, Midland, Mich.
Filed Jan. 17, 1975, Ser. No. 541,817
Int. Cl. A24f *25/00;* A61l *9/04*
U.S. Cl. 239—44
1 Sheet Drawing. 15 Pages Specification

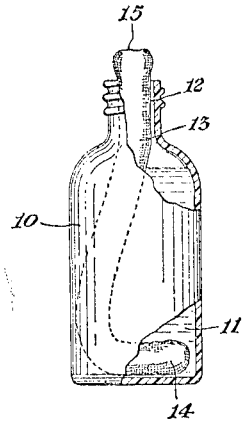

Insecticidal devices comprise a container, capable of holding liquid accessible to insects, composed of or containing plastic composition comprising an insecticidal agent capable of diffusing from the plastic composition to the liquid when the device is in use. Illustratively, at least the inside surface layer of the polyethylene bottle comprises a halopyridyl phosphate insecticide such as chlorpyrifos or fospirate; when charged with sugar water and fitted with a wick, the device is attractive and lethal to flies, mosquitos, roaches and the like.

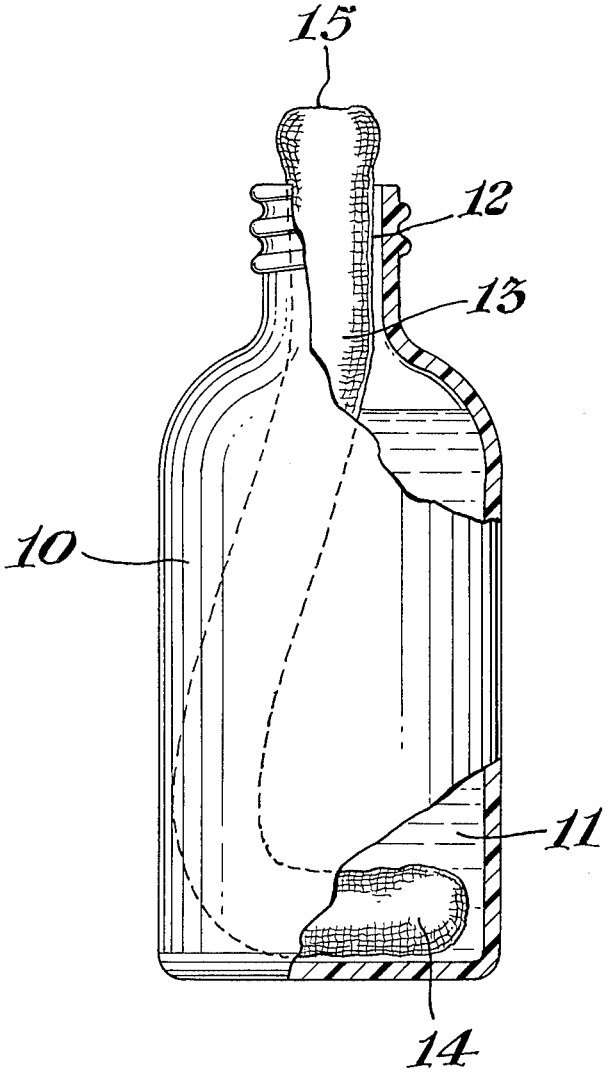

Dec. 2, 1975
F. H. DOWELL
INSECTICIDAL DEVICE
Original Filed Jan. 17, 1975
T941,025